United States Patent [19]

Nicolaou et al.

[11] 4,258,199

[45] Mar. 24, 1981

[54] METHOD FOR PREPARING CYCLIC ETHERS AND THIOETHERS INCLUDING OXYGEN ISOMERS AND SULFUR ANALOGS OF PROSTACYCLIN

[75] Inventors: Kyriacos C. Nicolaou, Philadelphia; William E. Barnette, Levittown, both of Pa.; Ronald L. Magolda, Vineland, N.J.; Zenon Lysenko, Philadelphia, Pa.

[73] Assignee: Research Corporation, New York, N.Y.

[21] Appl. No.: 886,143

[22] Filed: Mar. 13, 1978

[51] Int. Cl.$^3$ .................. C07D 333/78; C07D 307/93
[52] U.S. Cl. ................... 549/51; 260/346.22; 549/53
[58] Field of Search ............ 260/332.1, 332.2 A, 260/346.22; 549/51, 53

[56] References Cited

U.S. PATENT DOCUMENTS 3,881,017  4/1975  Vlattas .......................... 260/332.1

OTHER PUBLICATIONS

Corey, E. J. et al., "Synthesis of Vane's Prostaglandin X ...", J. Am. Chem. Society. (Communication) vol. 99 (Mar. 16, 1977), pp. 2006-2008.
Sharpless, K. B. et al., *J. Org. Chem.*, vol. 39 (1974) pp. 429-430.
C&EN (*Chemical & Engineering News*) Dec. 20, 1976, pp. 17-19.
Bundy, G. L. et al., *J. of the Am. Chem. Soc.*, vol. 94 (1972) p. 2124.
Royals, Earl E., *Adv. Org. Chemistry* (1963) p. 107.
Reid, E. Emmet, *Org. Chem. of Bivalent Sulfur* (1960) pp. 11, 12.
Brown, Herbert C., *Organometallics in Chemical Synthesis*, vol. 1 1970/1971, pp. 7-22.

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

Unsaturated alcohols, thiols and thioesters are cyclized by a phenyl selenenyl halide; wherein the conformation flexibility of the unsaturated alcohol, thiol or thioester is selected such that the hydroxy group, thiol group or thioester group is capable of internal addition to at least one unsaturated bond in said alcohol, thiol or thioester; and wherein the ratio of the phenyl selenenyl halide to said unsaturated alcohol, thiol or thioester is 0.9-1.5 to 1. In a preferred embodiment, oxygen isomers and sulfur analogs of prostacyclin of the formula

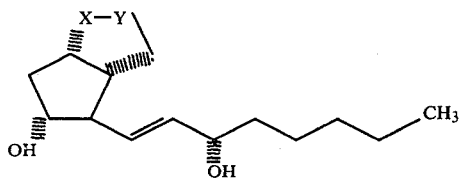

wherein
X =

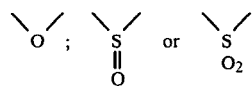

Y = (E)- and (Z)- >C=CH—CH$_2$CH$_2$CH$_2$COOR;
(E)- >CH—CH=CH—CH$_2$CH$_2$COOR; and
R = any pharmaceutically acceptable cation or lower alkyl group comprising 1 to 4 carbon atoms are formed by:

(1) cyclizing a PGF$_{2\alpha}$ prostaglandin derivative or a 9α thio or 9α-thioester analog of prostaglandin PGF$_{2\alpha}$ by reacting said prostaglandin derivative or analog with a phenyl selenenyl halide, wherein the molar ratio of said phenyl selenenyl halide to said prostaglandin derivative or analog is 0.9-1.5:1; and (2) oxidizing the product obtained therefrom.

26 Claims, No Drawings

METHOD FOR PREPARING CYCLIC ETHERS AND THIOETHERS INCLUDING OXYGEN ISOMERS AND SULFUR ANALOGS OF PROSTACYCLIN

BACKGROUND OF THE INVENTION

1. Field of the Invention

This invention relates to a method of preparing 5 to 7 membered cyclic ethers or thioethers by cyclization of unsaturated alcohols, thiols or thioesters with phenyl selenenyl halide. In a preferred embodiment, the invention also relates to a method of making oxygen and sulfur analogs of prostacyclin using the aforementioned synthetic methodology.

2. Description of the Prior Art

The importance of oxygen and sulfur heterocyclic compounds in the field of natural products has led to a demand for efficient synthetic methods to prepare these types of derivatives. Sulfur heterocycles are of importance in, for example, the β-lactam antibiotic field (Sammes, P., Chem. Revs. 76, 113 (1976)). Oxygen heterocyclic compounds, their sulfur analogs and derivatives thereof are important in the rapidly expanding field of prostacyclin research. Prostacyclin (I) is a recently discovered member of

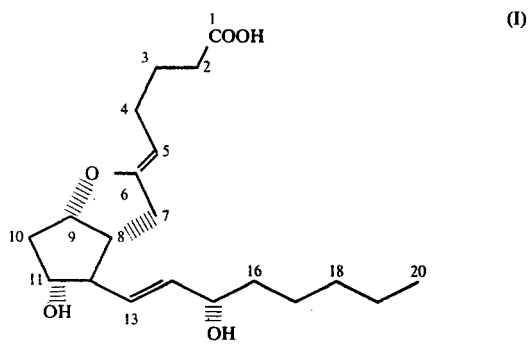

the family of prostaglandins (Vane, C. and En. News, Dec. 20, 1976). Its technical name is 6,9α-oxido-11α,1-5α-dihydroxyprosta-(Z)5, (E)13-dienoic acid. It is a cis-fused, bicyclic system which contains an acid-labile enol ether system. Prostacyclin has been involved in the regulation of blood platelet aggregation and the constriction and dilation of arteries. It is biosynthetically derived from its precursor, endoperoxide, which in turn is derived from the available pool of fatty acid precursors. The endoperoxide precursor also, generates, via another enzymatic system, a compound named thromboxane $A_2$, which shows opposite effects to prostacyclin. Both prostacyclins and thromboxanes exist in a delicate equilibrium and help to maintain the body balance of blood platelet aggregation versus dissolution, and arterial constriction versus dilation. Both compounds are hydrolyzed to prostaglandins.

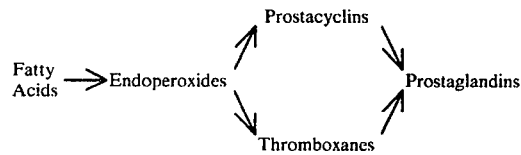

The use of prostacyclins has been suggested in the treatment of blood clotting in diseased vessels of patients with cardiovascular problems. Since prostacyclin has retroactive action and not only inhibits blood clotting but also dissolves already formed clots, it can be used in heart attack cases and artherosclerosis. Increased susceptibility of platelets to aggregation accompanies vascular complications in diabetes, in cerebral strokes associated with essential hypertension and in post heart infarct cases. These are other areas where prostacyclin activity can be highly beneficial. The main drawback of the use of prostacyclin for these applications is its very short biological half-life of 2 minutes. This prevents the externally provided drug from reaching its target tissues intact. The need to maintain the drug in a totally anhydrous condition also prevents its ready shipment, storage and testing for pharmacological applications. If an analog or derivative of prostacyclin can be formed which is stable and shows similar effects on blood platelets and arteries, it would have wide applications in pharmacology and the treatment of cardiovascular and related diseases.

There has emerged, with the discovery of prostacyclin, the need to prepare stable, pharmaceutically active isomers and analogs or derivatives thereof which can be used clinically. Sulfur analogs of prostacyclin are particularly promising in this respect. There has also emerged, as a consequence, the need to develop a general, mild, fast and synthetically useful method to prepare cyclic ethers, thioethers and their derivatives. Particularly useful for the prostacyclin field would be a method which could induce cyclization between the oxygen atom at position C-9 and carbon 6 of the readily obtained $PGF_{2\alpha}$ prostaglandin derivative of formula II (Given here with its standard numbering system):

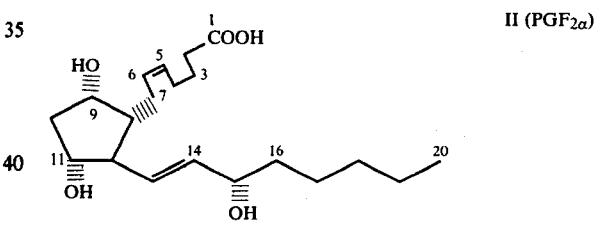

If in this formula, one replaced the hydroxy group at position 9 with a thiol or a thioester, and used the same cyclization methodology, one would have a general method of preparing prostacyclin-type derivatives and analogs. The problem thus consists of devising a mild method to cyclize unsaturated alcohols, thiols or thioesters.

It is known (Delmon, E., et al, Helvetica Chim. Acta., 54, 546 (1971)) to cyclize unsaturated alcohols with halogens to yield cyclic ethers. However, the reaction requires aqueous basic media which is incompatible with solubility properties and other functionalities present in the molecules being treated. In addition, the incompatibility of a rather large number of important functionalities and protecting groups with halogens decreases the area of applicability of this conventional procedure. It is also known to cyclize unsaturated alcohols and thiols using an acid or metal as a catalyst. (Brown, et al, Organometal. Chem. Synth., 1, 7 (1970)). The many acidlabile protecting groups or functionalities used in organic synthesis, limit this method to carefully selected cases where acid induced side reactions constitute no problem. The use of phenyl selenium reagents has recently been shown to be successful in the construction of open-chain allylic acetates and ethers from olefins (Sharpless, K. B., et al, J. Org. Chem., 39, 429 (1974)); of enones from ketones (Reich, H. J., et al, J. Amer. Chem. Soc., 97, 5434 (1975)). These precedents have led the inventors to investigate and develop the use of phenyl selenium reagents in the construction of cyclic ethers, thiols and their derivatives. Of particular interest is the use of these reagents in the construction of prostacyclin derivatives and analogs.

SUMMARY OF THE INVENTION

Accordingly, it is an object of the invention to develop an efficient and mild method for preparing cyclic ethers. Another object of the invention is to develop an efficient and mild method for preparing cyclic thioethers and derivatives thereof.

Still another object of the invention is to develop an efficient and mild method for preparing stable prostacyclin derivatives and/or isomers.

Yet another object of the invention is to develop an efficient and mild method for preparing stable sulfur analogs of prostacyclin and derivatives thereof.

A further object of the invention is to develop a method of making cyclic ethers, thioethers and derivatives thereof by using phenyl selenenyl halides.

Still a further object of the invention is to develop methods for preparing stable prostacyclin derivatives and their analogs which can be used pharmaceutically.

These and other objects of the invention which will become apparent hereinafter have been accomplished by cyclizing unsaturated alcohols, thiols and thioesters with a phenyl selenenyl halide; wherein the conformational flexibility of said unsaturated alcohol, thiol, or thioester is selected such that the hydroxy group, thiol group or thioester group is capable of internal addition with at least one unsaturated bond in said alcohol, thiol or thioester; and wherein the ratio of said phenyl selenenyl halide to said unsaturated alcohol, thiol or thioester is 0.9–1.5 to 1. In a preferred embodiment, oxygen isomers and sulfur analogs of prostacyclin of the formula

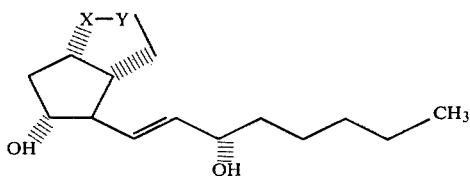

wherein
X =

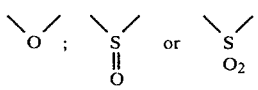

Y=(E)- and (Z)->C=CH—CH$_2$CH$_2$CH$_2$COOR;
(E)->CH—CH=CH—CH$_2$CH$_2$COOR; and R = any pharmaceutically acceptable cation or lower alkyl group comprising 1 to 4 carbon atoms are formed by:

(1) cyclizing a PGF$_{2\alpha}$ prostaglandin derivative or a 9α-thio or 9α-thioester analog of prostaglandin PGF$_{2\alpha}$ by reacting said prostaglandin derivative or analog with a phenyl selenenyl halide, wherein the molar ratio of said phenyl selenenyl halide to said prostaglandin derivative or analog is 0.9–1.5:1; and (2) oxidizing the product obtained therefrom.

Pharmaceutically acceptable cations useful for the purposes of this invention are those with pharmaceutically acceptable metal cations, ammonium, amine cations or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and loweralkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1, 3-propanediol, 2-amino-2-methyl-1-propanol, tris(hydroxymethyl) aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

Pharmaceutically acceptable lower alkyl groups are those derived from C$_1$–C$_{10}$ hydrocarbyl residues, especially C$_1$–C$_4$. Most preferred are methyl and ethyl groups.

DESCRIPTION OF THE PREFERRED EMBODIMENTS

The cyclization method of the present invention applied to prostacyclin derivatives is accomplished by reacting a PGF$_{2\alpha}$ derivative of formula III-Z or III-E (depending on the Z- or E-geometry about the C-5, C-6 double bond) with a phenyl selenenyl halide to yield the 5-phenyl seleno ethers of formula IV:

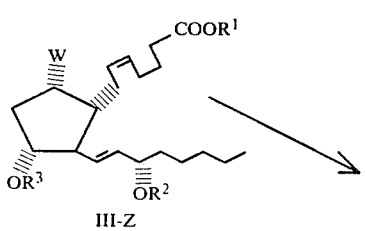

III-Z

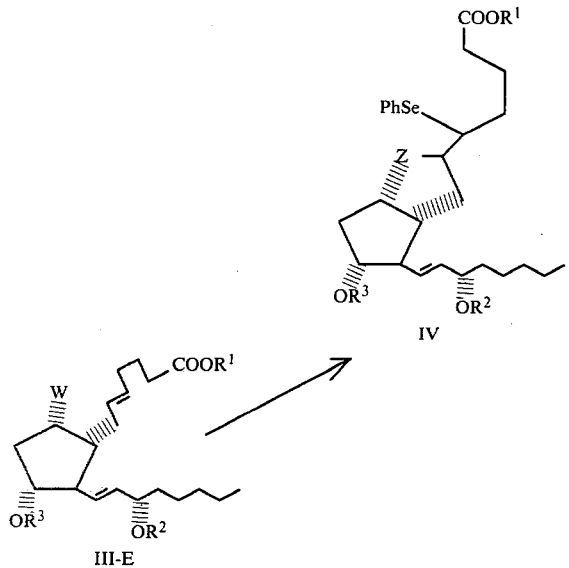

In these formulae, W represents —OH, —SH,

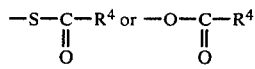

where $R^4$ represents a loweralkyl comprising 1 to 6 carbon atoms, preferably comprising 1 to 4 carbon atoms, most preferably R is —$CH_3$; $R^1$ is a carboxylic acid protecting group, such as a lower alkyl comprising 1–5 carbon atoms, preferably $R^1$ is methyl or ethyl, most preferably $R^1$ is methyl. $R^2$ and $R^3$ are H or hydroxy protecting groups and can be equal or different. These protecting groups are chosen so as to be compatible with the cyclization reaction, with the method of formation of precursors III-E and III-Z, with the subsequent treatment of product IV and with the object to provide for ease of deprotection under mild conditions. $R^2$ and $R^3$ can be base-labile groups, such as acetyl, trifluoroacetyl, trichloroacetyl, benzoyl or toloyl; they can be acid-labile groups such as tert-butyldimethylsilyl or tetrahydropyranyl. Z is

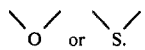

The useful phenyl selenenyl reagents are phenyl selenenyl bromide or chloride, most preferably chloride. Other selenenyl halides can be used, such as methylselenenyl halides, propylselenenyl halides, p-methylphenylselenenyl halides and halophenylselenenyl halides. Other selenium reagents can be used, such as phenylselenous acid (PhSeOH), phenylselenenylacetate (PhSeOAc) or phenylselenenyltrifluoroacetate

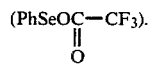

The reaction may be carried out in the absence of oxygen, in which instance, the reaction mixture is degassed by standard degassing techniques and run under vacuum or under an insert atmosphere. Gases such as nitrogen or rare gases such as helium and argon can be used to provide an inert atmosphere. The products of the cyclization reaction, cyclic thioethers of formula IV, are purified by standard techniques, well-known to those skilled in the art. These techniques include high pressure liquid chromatography, silica gel column chromatography, alumina gel column chromatography, thin layer chromatography and preparative gel chromatography. The solvents useful in this cyclization reaction are alcohols, such as methanol, ethanol, propanol and isopropanol; inert organic solvents such as halogenated hydrocarbons, e.g., methylene chloride, chloroform, carbon tetrachloride or dichloroethane; ethers such as diethyl ether, di-isopropyl ether, tetrahydrofuran and mixtures thereof. Preferred solvents are methylene chloride and tetrahydrofuran, most preferred is methylene chloride. The reaction temperature depends on the nature of the starting materials and solvents, but may be as low as −78° C. or as high as 25° C. Preferably the temperature is −78° C. to −20° C. The length of the reaction ranges from 10 minutes to 3 hours. Preferably the length of the reaction is from 15 mins. to 2 hr; most preferred is 30 mins.

When W in formulae III is a thiol or thioester derivative (supra) it is observed that the ring closure to IV proceeds equally well when the thioester (W=—S—CO—$R^4$) is utilized as when the thiol is utilized (W=—SH). This observation is synthetically important since it allows the cyclization to take place from a stable, protected form of the usually rather labile, unsaturated thiols such as III-Z or III-E. In some cases it is preferred to treat the thioester with a base to produce the free thiol and then rapidly add the phenyl selenenyl halide reagent to promote cyclization. This sequence of events also prevents unwanted complications due to the lability of the free thiols.

When W=—OH, the starting materials for the cyclization reaction, III-Z and III-E, are simply 5(Z) and 5(E) $PGF_{2\alpha}$ derivatives. When W=—SH or

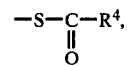

the starting materials for the cyclization reaction, III-Z and III-E, can be prepared by the following sequence of reactions from common intermediate V-Z:

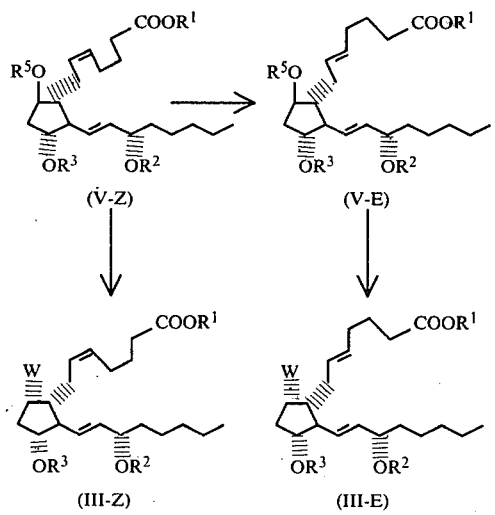

Since the III-Z and III-E derivatives ($R^1$, $R^2$, $R^3$=appropriate protecting groups, supra) are simple double bond isomers of each other, it is possible to produce either from V-Z ($R^5$=appropriate protecting group, infra), which is a 5(Z), 9α -oxy $PGF_{2\alpha}$ ester derivative. The preparation of V-Z can be made by a variety of reactions, infra. The transformation of V-Z (cis isomer at C-5) into V-E (trans isomer at C-5) can be carried out by standard double bond isomerization reactions, well known to those skilled in the art. Such reactions include, for example, photochemical isomerization.

The photochemical transformation of V-Z (5-cis isomer) to V-E (5-trans isomer) is carried out using well known photochemical techniques. The protecting groups for the starting material are chosen so as to minimize side reactions and allow easy recovery of final products. $R^5$ is preferably a group that will render the resulting 9β-oxy derivative reactive towards nucleophilic substitution reactions by sulfur nucleophiles; in other words, the resulting $R^5$O-group should be a good leaving group, preferably better in leaving ability than the $R^2$O- and $R^3$O-groups. Examples of functions that can be used for $R^5$ include, but are not limited by, organic sulfonyl derivatives, organic phosphoryl derivatives, and organic phosphonyl derivatives. Preferred $R^5$ groups are organic sulfonyl derivatives, most preferred is p-toluenesulfonyl or methane sulfonyl

or $CH_3—SO_2—$). The appropriately protected starting 5(Z), 9α-oxy $PGF_{2\alpha}$ alkyl ester derivative (V-Z) can be easily prepared from the deprotected precursors by well known reactions. In order to impart selectivity in the introduction of the $R^2$, $R^3$ and $R^5$ groups, these groups are introduced at different times during the formation of the intermediate V-Z. The sequence and order to introduction of the protecting groups will be discussed infra, when describing the synthesis of V-Z itself. The photochemical isomerization of V-Z into V-E is carried out in inert organic or inorganic solvents such as water, alcohols such as methanol or ethanol, hydrocarbons such as benzene or toluene, or polar aprotic solvents such as DME, DMF, DMSO, acetonitrile. Preferred solvents are benzene or toluene, most preferred is benzene. The reaction can be carried out in the presence of a free radical initiator such as diphenyldisulfide or dibenzoylperoxide. The most preferred initiator is diphenyldisulfide. The reaction is carried out in the absence of oxygen, under vacuum or in the presence of an inert gas such as nitrogen, or rare gases. Most preferred is to carry out the reaction in a degassed solution. The temperature of the reaction can be in the range of from −50° C. to +30° C., preferred range is 0° to 25° C., most preferred temperature is 20° C. The ratio of starting material V-Z to free radical initiator is from 1:0.1-1, preferred 1:0.1-0.6, most preferred is 1:0.5. The length of the reaction is in the range 1-15 hours, preferably 2 to 6 hours, most preferably 4 hours. Irradiation is done with standard commercial photochemical equipment, at wavelengths in the ultraviolet range. After the reaction has proceeded for the chosen length of time, there is obtained an equilibrium mixture of 5(E), 9β-oxy and 5(Z), 9β-oxy $PGF_{2\alpha}$ alkyl ester derivatives (V-E and V-Z), with the 5(E) isomers usually predominating.

The separation of the 5(E) and 5(Z) isomers, carried out in order to obtain pure V-E and to recover starting V-Z for recycling purposes can be done by standard purification techniques. The most preferred technique is a silver nitrate-impregnated silica gel column. The yield of 5(E) isomer V-E is 60-90%, usually about 80% and the purity is satisfactory.

The photochemical isomerization of the C-5 double bond can be carried out at the level of isomer III-Z. The reaction is not dependent on the exact configuration around asymmetric centers at C-9, C-11 and C-15 and can be carried out on any configuration of said asymmetric centers or combinations thereof.

For other, similar photochemical isomerizations in the prostaglandin field see, for example, Corey, et al (Tetr. Letters, 3529 (1977), and Schneider, et al (J. Amer. Chem. Soc., 99, 1222 (1977)).

The transformation of isomers V into isomers III(W= —SH or

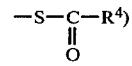

involves a nucleophilic displacement reaction by a sulfur nucleophile with inversion at carbon C-9 of V, to change its configuration from 9β to 9α. This nucleophilic displacement reaction is independent of the configuration of the double bond at C-5 so that the reaction can be described once for both IV-Z and IV-E isomers. The sulfur nucleophile used in the reaction includes thioacyl derivatives of the formula

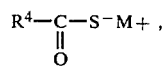

where $R^4$ is alkyl such as methyl, ethyl or propyl, aryl such as phenyl, toloyl and M+ is an alkali metal cation such as Na+, K+, Li+. Preferred nucleophilic reagents are potassium salts, most preferred reagent is potassium thioacetate ($CH_3COSK$). The ratio of starting material V to thioacylate nucleophile is 1:20, preferably 1:10, most preferably 1:5. The transformation V→III is carried out in polar solvents which are conducive to $SN_2$ reactions; preferred solvents are polar aprotic solvents such as DMSO, DMF, HMPA, acetonitrile, most preferred solvent is DMSO. The temperature of the reaction is in the range 25°-80° C., preferred range is 30°-50° C., most preferred temperature is 45° C. The length of the reaction time is in the range of 12 hours to 2 days, preferably 24 hours. The yield is excellent in most cases, 85% or better.

Intermediate V-Z which is an appropriately substituted 5(Z), 9αoxy $PGF_{2\alpha}$ alkyl ester derivative can be readily obtained from an appropriately protected $PGE_2$ alkyl ester such as VI-Z or an appropriately protected $PGF_{2\alpha}$ alkyl ester.

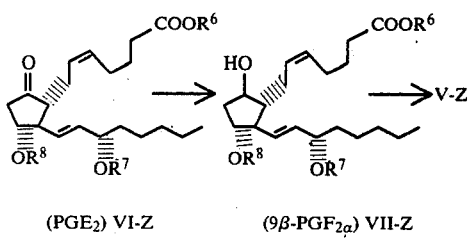

(PGE$_2$) VI-Z     (9$\beta$-PGF$_{2\alpha}$) VII-Z

Precursor VI-Z (R$^6$=—CH$_3$, R$^7$=—COCH$_3$, R$^8$=H) can be prepared by a known literature method (Corey et al, Proc. Nat. Acad. Sci., 72, 3355 (1975); Bundy et al, J. Amer. Chem. Soc., 94, 2123 (1972)). The groups R$^6$, R$^7$ and R$^8$ however, need not be limited to those described in the aforementioned references, but may be any of those described supra for the intermediate V-Z. It is useful to protect the C-11 hydroxy position with an acetyl or tetrahydropyranyl (THP) group, preferably tetrahydropyranyl. The reduction of the appropriately protected PGE$_2$ derivative VI-Z to the PGF$_{2\alpha}$ derivative VII-Z is carried out using standard reduction reagents and techniques. Reducing agents such as NaBH$_4$ or Zn(BH$_4$)$_2$ can be used, preferably Zn(BH$_4$)$_2$. The solvents, reaction temperatures, reaction times, and reactant ratios are well described in the organic literature and will not be further discussed. The product of the reduction is VIII-Z; it is obtained as a mixture of 2 diastereomers $\alpha$ and $\beta$ with opposite configurations at C-9. The ratio of 9$\alpha$ (undesired isomer) to 9$\beta$ (desired isomer) is about 1:1 and the total yield is usually better than 95%. The 9$\alpha$ and 9$\beta$ isomers can be separated by chromatographic techniques such as those described supra for the separation of V-Z from V-E. Finally, the partially protected PGF$_{2\alpha}$ derivative VII-Z is transformed to the fully protected derivative V-Z by reaction with an organic sulfonyl halide such as mesylchloride or tosylchloride. The reaction of hydroxy derivatives with acyl halides is well known in the art and will not be described further. (Crossland, R., et al, J. Org. Chem., 35, 3195 (1970)). Another method of preparing the required precursor V-Z is to use the well known PGF$_{2\alpha}$ alkyl ester derivatives such as 11,15-bis(THP) ether PGF$_{2\alpha}$ methyl ester as starting material, (Corey et al, J. Amer. Chem. Soc., 92, 397 (1970)). The transformation of this material to the desired PGF$_{2\alpha}$ derivative V-Z is by epimerization at carbon C-9 from the $\alpha$ to the $\beta$ configuration. As described supra, the protecting groups R$^1$, R$^2$ and R$^3$ need not be limited to those described in the Corey et al reference, but may be chosen from a larger number.

The epimerization of the C-9 carbon from 9$\alpha$ to 9$\beta$ configuration is carried out by first transforming the 9 hydroxy group of 11,15-bis(THP)-PGF$_{2\alpha}$ methyl ester to a good leaving group, preferably a mesylate, using the acyl chloride method under standard esterification conditions supra. The C-9$\alpha$-center is then transformed to the C-9$\beta$-hydroxy derivative VII-Z using the known technique of displacement with potassium superoxide (Corey et al, Chem. Comm., 658 (1975)). The VII-Z derivative is then transformed by acylation with mesyl or tosyl chloride to the V-Z derivative; a bis-11,15-(THP) ether, 9$\beta$-mesylate PGF$_{2\alpha}$ methyl ester.

If it were necessary to change the protecting groups on intermediate V-Z before continuing to V-E by photochemical isomerization or to III-Z by thioacylate replacement, the deprotection/reprotection intermediate steps can be carried out easily by following standard practice in the field of organic chemistry.

The selenoether IV is reacted with an oxidizing agent to yield an unsaturated cyclic ether. The conditions of oxidation vary according to the nature of the group Z and to the nature of the desired final product. When Z=

the cyclic selenoether of formula IV is reacted with an oxidizing agent such as 30% hydrogen peroxide to yield a syn type elimination away from the oxygen. The product is thus an allylic or $\beta$-$\gamma$-unsaturated cyclic ether (VIII), shown here in the 4(E) configuration.

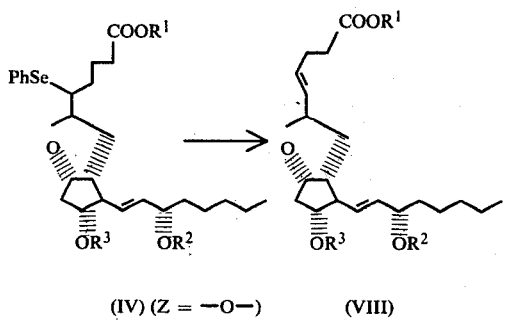

(IV) (Z = —O—)     (VIII)

The oxidation of open chain selenoethers to yield allylic open-chain ethers has been described by Sharpless et al (supra). The solvent can be chloroform, methylene chloride, DME, or THF. Preferred solvent is methylene chloride or THF; the most preferred solvent is THF. The ratio of oxidizing agent to starting material IV is usually 10-1:1, preferably 2.5-1:1, most preferably 1.1:1. The temperature of the reaction is from $-20°$ C. to $+30°$ C., preferably 0°-25° C. The most preferred method of carrying out the oxidation is by starting the reaction at about 0° C. and allowing the mixture to come to room temperature (about 25° C.) as the reaction progresses.

When Z=>S, the cyclic selenoether of formula IV is also oxidized but under various conditions, ranging from mild to strong, depending on the degree of oxidation desired in the product.

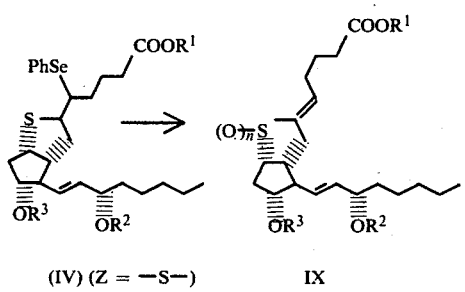

(IV) (Z = —S—)     IX wherein n=1 or 2.

The production of the (Z)-vinylic sulfoxide or sulfone IX is shown above only as example. The value of n depends on the the nature and strength of the oxidizing agent. The strict syn stereoselectivity of the elimination reaction determines the formation of (Z)-sulfoxide or sulfone from (E)-starting materials (III-E) and the formation of (E)-sulfoxide or sulfones from (Z)-starting materials (III-Z). The elimination of the phenyl selenenyl group caused by the oxidizing agent normally occurs to yield the vinylic (or α-β unsaturated) sulfoxides or sulfones. This is opposite to the case with oxygen selenoethers, which as described supra, yield only the allylic (or β-γ unsaturated) cyclic ethers. Since the oxidation agent reacts with both the sulfur and the selenium atoms at different rates, it is possible, by choosing the correct conditions of oxidizing agent and temperature, to impart a high degree of selectivity onto the oxidation reaction. The oxidation reaction to yield the sulfoxide isomers is carried out with close to equivalent (1.1) amounts of a selective mild oxidizing agent such as m-chloroperbenzoic acid (MCPB) at low temperatures −78° to −20° C. The formation of the sulfone is carried out with a slight excess of MCPB (2.2 equiv.) at low temperatures, preferably starting at −78° C. and finishing at +25° C., followed by excess of a non-selective oxidizing agent such as $H_2O_2$ at close to room temperature for 24 hours. This sequence of reactions yields the vinylic α-β-unsaturated sulfone. When an excess of $H_2O_2$ (8–10 equivalents) was used at 25° C., the product was a mixture of α-β- and β-γ-unsaturated sulfones. When stoichiometric amounts of $H_2O_2$ were used at 0° C., a mixture of α-β- and β-γ-unsaturated sulfoxides was obtained, together with α-β- and β-γ-unsaturated sulfones. Thus, by changing the geometry of the starting unsaturated thiol or thiol derivative (III-E or III-Z, W =

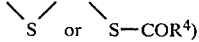

and by changing the nature of the oxidizing agent, it is possible to obtain (E) and (Z), α-β- or β-γ-unsaturated sulfoxides or sulfones.

It should be further noted that when n = 1 in compound IX (or its (E-) isomer), the compound exists as one pair of 2 distinct diastereomers due to the rigid nature of the sulfoxide sulfur-oxygen bond. These 2 isomers can be isolated and purified by standard analytical techniques. In the case of the β-γ-unsaturated (allylic) sulfone or oxygen ether, the C-6 center exists in 2 epimeric configurations which generate, for each of these derivatives, a pair of distinct, separable diastereomers.

The removal of the protecting groups $R^1$, $R^2$ and $R^3$ from the resulting products of the oxidation, i.e, the allylic oxygen cyclic ethers or sulfones or the vinylic sulfoxides, or sulfones, can be carried out with acid or base or sequentially with both, if necessary, and yields prostacyclin isomers and analogs. A particularly useful prostacyclin sulfur analog, 6,9α-thiaprostacyclin ester can be obtained by reducing a 6,9α-sulfoxaprostacyclin ester—obtained as described supra—with a reducing agent such as trimethylsilyliodide. The prostacyclin isomers and sulfur analogs of the present invention are more stable in solution than the natural prostacyclin I. (Table I).

Pharmacological testing of the prostacyclin isomers and/or analogs of the present invention has shown that they are useful as inhibitors of blood platelet aggregation, as antagonists for natural prostacyclin and have biological effects on cat coronary artery.

The thio analogs of the present invention can also be used as inhibitors of platelet aggregation of externally circulated blood in patients treated with kidney dialysis machines or heart lung machines.

| Product | t ½ saline 250° C. | Biological Activity | |
|---|---|---|---|
| | | Platelet Aggregation | Cat Coronary Artery |
| Natural Prostacyclin | 2 minutes | Inhibitor(P) | Dilator(P) |
| 4(E)-9-deoxy-6,9α-epoxy-Δ⁴-isoprostacyclin(6α) | >3 hours | Antagonist | Constrictor |
| 4(E)-9-deoxy-6,9α-epoxy-Δ⁴-isoprostacyclin(6β) | >3 hours | Inhibitor(P) | Constrictor(P) |
| 6,9α-Thia-5(Z)prostacyclin | >3 hours | Very little activity, if any | Very little activity, if any |
| 6,9-sulfoxa-5(E)prostacyclin | >24 hours | Little activity | Little activity |
| 6,9-sulfoxa-5(Z)prostacyclin | >24 hours | Little activity | Little activity |
| 6,9-sulfo-5(Z)prostacyclin | >24 hours | Antagonist(M) | Constrictor(M) |
| 6,9-sulfo-4(E)isoprostacyclin, 6α isomer | >24 hours | Inhibitor | Constrictor(M) |
| 6,9-sulfo-4(E)isoprostacyclin, 6β isomer | >24 hours | Antagonist | Constrictor |

P = Potent
M = Moderate (in concentrations $10^{-6}$ molar)
Very little activity means at concentrations $<10^{-6}$M; compounds may show more activity at concentrations $>10^{-6}$M.

Effects of prostacyclin analogs on platelet aggregation was evaluated using human and rabbit citrated platelet-rich plasma in a chronolog aggregometer at 370°. Each of the analogs was tested at two concentrations (20 mM and 2 μM) for agonistic activity (inhibition of aggregation induced by 2 μM ADP) and antagonistic activity (prevention of the inhibition of ADP-induced aggregation by 5 mM prostacyclin).

Effects of prostacyclin analogs on isolated perfused cat coronary arteries were measured as follows.

Cats of either sex (2.5–3.5 kg) were anesthetized with sodium pentobarbital (30 mg/kg) given intravenously. Hearts were rapidly excised and placed in oxygenated (95% $O_2$+5% $CO_2$) ice-cold Krebs-Henseleit (K-H) solution of the following millimolar composition: NaCl, 118; KCl, 4.75; $CaCl_2.H_2O$, 2.54; $KH_2PO_4$, 1.19; $MgSO_4.7H_2O$, 1.19; $NaHCO_3$, 12.5; glucose, 10.00. A 20-gauge stainless steel cannula was inserted into the right coronary artery via the coronary ostium. Distal to the cannula, approximately 1 cm of coronary artery was dissected free of surrounding tissue. The section of right coronary artery with the cannula in place was excised from the heart and immediately transferred to a constant flow perfusion apparatus.

The perfusion apparatus consists of a reservoir containing 20 ml of warm (37° C.) oxygenated (95% $O_2$+5% $CO_2$) K-H solution which bathes the coronary artery and serves as recirculating perfusate. An increase in perfusion pressure indicates vasoconstriction, whereas a decrease in perfusion pressure signifies vasodilation. Following an initial 1 hr. equilibrium period, vascular responsiveness was established by adding 25 mM KCl. After washing with fresh K-H solution for 20–30 mins., the preparation achieved a relatively constant low basal tone. Basal perfusion pressure averaged 50±2.5 mm Hg. Fresh K-H dilutions of stock prostacyclin analog concentrations were added to the perfusate reservoir in 0.1–0.2 ml volumes. Changes in perfusion pressure in response to prostacyclin analog addition generally plateaus within 5 mins. of administration. Results are summarized in Table 1.

The 4(E) oxygen isomers show biological activity.

The sulfur analogs of the 5(Z) configuration generally show bioactivity in vitro while the sulfur analogs of the 5(E) configuration do not. The biological activity itself is an unexpected combination of effects. While all of the active sulfur analogs show inhibition or antagonist activity to blood platelet aggregation as seen with natural prostacyclins, they also show powerful vasoconstrictor activities, as seen with natural thromboxanes or endoperoxides. The combination of these biological effects render the sulfur analogs of prostacyclins as useful in the treatment of platelet clump dissolution, treatment of thrombosis, treatment of artherosclerosis, treatment of vascular complications in diabetes, hypertension, hypotension, kidney dialysis and heart lung machines, and other related uses.

The compounds of this invention can be administered by any means that effects palliating conditions of cardiovascular complications in warm-blooded animals. For example, administration can be parenterally, subcutaneously, intravenously, intramuscularly or intraperitoneally. Alternatively or concurrently, administration can be by the oral route. The dosage administered will be dependent upon the age, health and weight of the recipient, kind of concurrent treatment if any, frequency of treatment, and the nature of the effect desired. Generally, daily dosage of active ingredient compounds will be from about 0.5 to 50 mg per kg of body weight. Normally, from 1 to 30 mg per kg per day, in one or more applications per day is effective to obtain the desired result. The compounds can be employed in dosage forms such as tablets, capsules, powder packets, or liquid solutions, suspensions, or elixirs, for oral administration, or sterile liquid formulations such as solutions or suspensions for parenteral use. In such compositions, the active ingredient will ordinarily always be present in an amount of at least 0.5% by weight based on the total weight of the composition and not more than 90% by weight.

The use of the phenyl selenium halide methodology to induce cyclizations in unsaturated alcohols and unsaturated thiols or thioesters has also been extensively investigated by the inventors. The results are all in accordance with those described supra for the prostacyclin derivatives. Cyclic oxygen selenoethers are formed by phenylselenenyl halide-induced cyclization of unsaturated alcohols; further reaction of these seleno cyclic ethers with oxidizing agents, yields β,γ-unsaturated (allylic) cyclic ethers. Cyclic thioselenoethers are formed by phenylselenenyl halide-induced cyclization of unsaturated thiols or unsaturated thiol esters; oxidation under selective conditions yields α,β-unsaturated (vinylic) cyclic sulfoxides and sulfones; oxidation under non-selective conditions yields mixtures of α,β- and β,γ-unsaturated cyclic sulfones and sulfoxides. The stereochemical considerations described supra for the prostacyclin case apply equally well for the case of general cyclization reactions.

Most 5- and 6-membered cyclic ethers and thioethers can readily be made using the phenyl selenium halide cyclization methodology. The reaction, however, does not work in all cases. There is a strong preference for low energy, low-strained transition states when possible; in cases where the geometry of the substrate is not favorable for ring closure and/or the expected product would be severely hindered, the reaction leads to uncyclized products. Thus, while alcohol X readily cyclizes to phenyl selenoether XI, thioacetate XII only yields uncyclized product XIII.

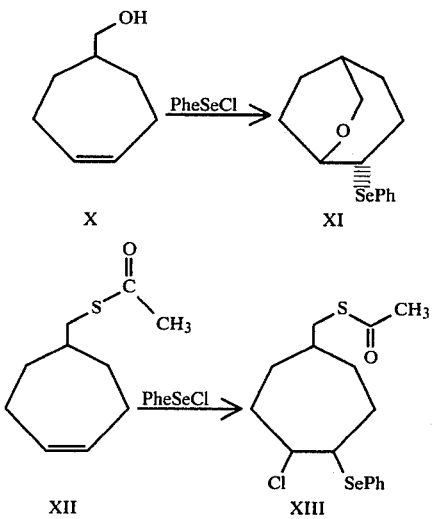

As a further example, when diol XIV is treated with PheSeCl, only the 1-hydroxy group reacts to give cyclization, although both hydroxy groups would give 5-membered cyclic transition states:

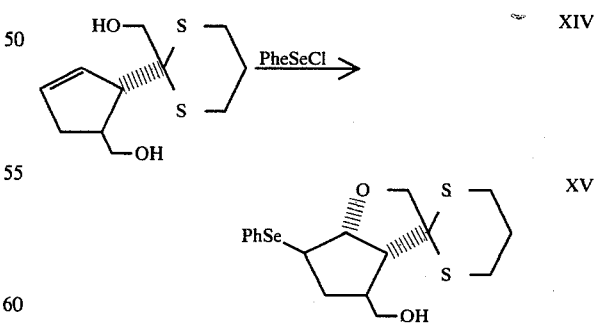

Table II gives a list of examples of cyclic ethers or thioethers prepared by the cyclization method of the present invention. The examples will now be discussed in detail and are not intended to be limitative of the invention.

TABLE II

ORGANOSELENIUM-INDUCED CYCLIZATIONS OF UNSATURATED ALCOHOLS, THIOLS AND THIOACETATES

| | Starting Material | Product | (%) Overall Yield |
|---|---|---|---|
| (1) | cyclohexene-CH$_2$OH | bicyclic ether with SePh | 87 |
| (2) | HO-C(S(CH$_2$)$_3$S)-cyclopentene-CH$_2$OR$^9$ | PheSe-cyclopentane-O-C(S(CH$_2$)$_3$S)-CH$_2$OR$^9$ | 86 (R$^9$ = $^t$Bu(CH$_3$)$_2$Si-)  90 (R$^9$ = H) |
| (3) | R$^{10}$S-cyclopentane-CH=CH-CH$_3$ | SePh-CH(CH$_3$)-S-cyclopentane | 85 (R$^{10}$ = H)  80 (R$^{10}$ = C(O)CH$_3$) |
| (4) | AcS-cyclopentane-CH=CH-CH$_3$ | CH$_3$-CH(SePh)-S-cyclopentane | 88 |
| (5) | cyclohexene-CH$_2$CH$_2$-SAc | SePh-bicyclic-S | 77 |
| (6) | norbornene-AcS | PhSe-norbornane-S | 81 |
| (7) | RS-cyclopentane-CH=CH-(CH$_2$)$_3$COOCH$_3$ | SePh-CH-(CH$_2$)$_3$COOCH$_3$, S-cyclopentane | 81 (R = H)  77 (R = C(O)CH$_3$) |
| (8) | AcS-cyclopentane-CH=CH-CH$_2$-COOCH$_3$ | cyclopentane-S-CH(SePh)-CH$_2$COOCH$_3$ | 80 |
| (9) | HO-cyclopentane(OH)(CH=CH-CH(OH)-C$_5$H$_{11}$)-CH$_2$CH=CH(CH$_2$)$_3$COOCH$_3$ | PhSe-CH-(CH$_2$)$_3$COOCH$_3$, O-cyclopentane(OH)(CH=CH-CH(OH)-C$_5$H$_{11}$) | 80 |
| (10) | RS-cyclopentane(OH)(CH=CH-CH(OH)-C$_5$H$_{11}$)-CH$_2$CH=CH(CH$_2$)$_3$COOCH$_3$ | PhSe-CH-(CH$_2$)$_3$COOCH$_3$, S-cyclopentane(OH)(CH=CH-CH(OH)-C$_5$H$_{11}$) | 80 (R$^{10}$ = H) |

TABLE II-continued
ORGANOSELENIUM-INDUCED CYCLIZATIONS OF UNSATURATED ALCOHOLS, THIOLS AND THIOACETATES

| Starting Material | Product | (%) Overall Yield |
|---|---|---|
| (11) | | 75% |

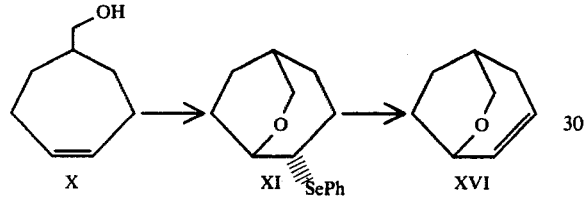

$R^{10} = $ —H or $\overset{\overset{O}{\|}}{\underset{}{\diagup}}CH_3$

EXAMPLE 1a
Preparation of bicyclo allylic ether XVI:

4-Cycloheptene-1-methanol(X) (Hendrickson, et al, J. Org. Chem. 36, 2315 (1971), on treatment with PhSeCl (1.1 equiv.) in $CH_2Cl_2$ at $-78°$ afforded, after column chromatography, ($SiO_2$; $CH_2Cl_2$) the phenylselenoether XI in 95% yield as a colorless oil, NMR (CDCl$_3$; 220 MHz) τ2.52 (m, 2H, Ph), 2.80 (m, 3H, Ph), 6.04 (m, 1H, $-\overset{|}{O}CH-$), 6.16 and 6.35 (doublets, J=4 Hz, 1H each, $-OC\underline{H}_2-$), 6.47 (m, 1H, $-\overset{|}{S}eCH-$), 7.70-8.50 (m, 9H, $-\overset{|}{C}H_2-$ and $-C\underline{H}-$). Oxidation of the phenylseleno group of XI with 30% hydrogen peroxide (1.5 equiv.) in THF at 0°-25° afforded, by syn elimination, the allylic ether XVI in 87% yield, m.p. 60°-61° (sublimed), NMR (CDCl$_3$, 220 MHz) τ4.04 and 4.21 (multiplets, 1H each, olefinic), 5.85 (m, 1H, $-\overset{|}{O}CH-$), 5.98 and 6.14 (multiplets, 1H each, $-OC\underline{H}_2-$), 7.30-8.35 (m, 7H, $-C\underline{H}_2-$ and $-\overset{|}{C}H-$).

EXAMPLE 1b
Preparation of bicyclo ether XVII:

Reductive removal of the phenylseleno group from intermediate XI of example 1a by Raney Nickel in THF at 25°0 proceeded cleanly to furnish the bicyclic saturated ether XVII in 94% yield, purified by sublimation, m.p. 119°-120°, NMR (CDCl$_3$, 220 MHz) τ5.96 (m, 1H, $-\overset{|}{O}CH-$), 6.05 and 6.25 (broad doublets, J=4, 5 Hz, 1H each, $-OC\underline{H}_2-$), 7.80-8.50, (m, 11H, $-C\underline{H}_2-$ and $-\overset{|}{C}H-$).

EXAMPLE 2a
Preparation of allylic ether XX:

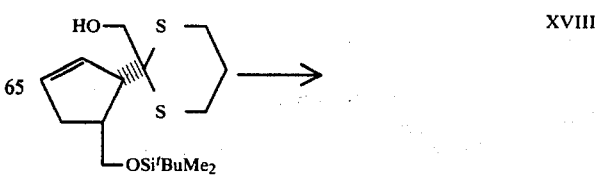

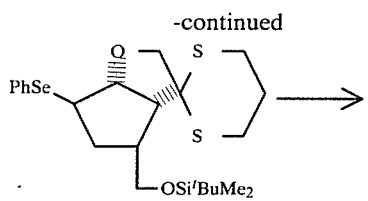

The generality and applicability of this new etherification reaction in complex and sensitive cases was tested by the conversion of the unsaturated alcohol XVIII to its corresponding ether. Reaction of XVIII with PhSeCl (1.1 equiv.) in CH$_2$Cl$_2$ at −78° produced rapidly the 5-membered ring ether XIX isolated by column chromatography (SiO$_2$; CH$_2$Cl$_2$) in 86% yield, m.p. 76°-77° (pentane). The structure was based on its NMR spectrum, (CDCl$_3$, 220 MHz) τ2.45 (m, 2H, Ph), 2.74 (m, 3H, Ph), 5.26 (dd, J=3, 2 Hz, 1H, $$-\text{OCH}-),$$

5.79 and 6.06 (doublets, J=4 Hz, 1H each, —OC$\underline{H}_2$—), 6.22 (dd, J=4.5, 2 Hz, 1H, $$-\text{SeCH}-),$$

6.43 (m, 2H, $$-\text{CH}_2\text{OSi}-),$$

7.16 (m, 4H), 7.27 (t, J=3 Hz, 1H), 7.64 (m, 2H), 8.00 (m, 2H), 8.30 (m, 1H) (—C$\underline{H}_2$— and $$-\text{CH}-),$$

9.10 [s, 9H, $$-\text{Si(CCH}_3)_3],$$

9.93 [s, 6H, $$-\text{Si(CH}_3)_2]$$

and its transformation (1.5 equiv. H$_2$O$_2$ in THF at 0°-25°; 75%) to the unsaturated ether XX, NMR (CDCl$_3$, 220 MHz) τ4.10 and 4.30 (multiplets, 1H each, olefinic), 4.68 (m, 1H, $$-\text{OCH}-);$$

5.90 and 6.43 (doublets, J=4 Hz, 1H each, —OC$\underline{H}_2$—), 6.47 d, J=3 Hz, 2H, $$-\text{CH}_2\text{OSi}-),$$

6.72 (m, 1H), 7.15 (m, 5H), 7.98 (m, 2H) (—C$\underline{H}_2$— and $$-\text{CH}-),$$

9.12 [s, 9H, —Si—C(C$\underline{H}_3$)$_3$], 9.95 [s, 6H, $$-\text{Si(CH}_3)_2].$$

EXAMPLE 2b

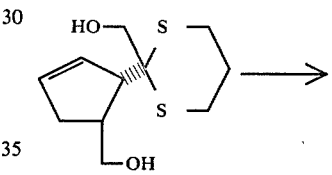
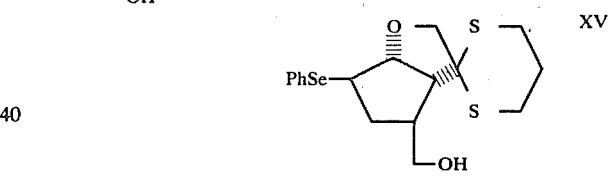

An interesting observation was made when the diol XIV was subjected to the cyclization reaction as described above. Thus, on exposure to PhSeCl, the ether XV was formed exclusively in 90% yield, NMR (CDCl$_3$, 220 MHz) τ2.47 (m, 2H, Ph), 2.74 (m, 3H, Ph), 5.24 (dd, J=3, 2 Hz, 1H, $$-\text{OCH}-),$$

5.78 and 6.05 (doublets, J=4 Hz, 1H each, —OC$\underline{H}_2$—), 6.20 (dd, J=4.5, 2 Hz, 1H, $$-\text{SeCH}-),$$

6.37 (m, 2H, —C$\underline{H}_2$OH), 7.50 (s, 1H, O$\underline{H}$), 7.12 (m, 4H), 7.54 (m, 2H), 8.00 (m, 2H) and 8.30 (m, 1H) (—C$\underline{H}_2$— and $$-\text{CH}).$$

Silylation of XV gave a material chromatographically and spectroscopically identical to XIX (example 2a) establishing the skeletal structure assigned to XV.

EXAMPLE 3a

Thiol XXI ($R^{10}$=H) reacted rapidly with PheSeCl at −78°→25° C. in dry methylene chloride to afford the cyclic thioether XXII in 80% yield. It was isolated by extraction and purified by preparative thin layer chromatography; m.p.-oil.

EXAMPLE 3b

Thioester XXI ($R^{10}$=

$$-\overset{O}{\underset{\|}{C}}-CH_3)$$

reacted with PhSeCl at −35° C. in acetonitrile to afford the cyclic thioether XXII in 75% yield. It was isolated by extraction and purified by preparative thin layer chromatography.

EXAMPLE 3c

Thioester XXI ($R^{10}$=

$$-\overset{O}{\underset{\|}{C}}-CH_3)$$

reacted with PhSeCl at −78° C. in methanol to afford the cyclic thioether XXII in 85% yield. It was isolated by extraction and purified by preparative thin layer chromatography.

EXAMPLE 3d

Thioester XXI ($R^{10}$=

$$-\underset{\underset{O}{\|}}{C}CH_3)$$

reacted with PhSeCl at −78° C. in dry methylene chloride to afford the cyclic thioether XXII in 80% yield. It was isolated by extraction and purified by preparative thin layer chromatography.

EXAMPLE 3e

When the phenylselenothioether XXII was exposed to excess $H_2O_2$ (8 equiv.) in THF at 25° C. for 24 hours a mixture of (E)-2,3-unsaturated sulfone and the 1,2-unsaturated sulfone isomer were obtained in 92% yield. (Ratio 2,3:1,2-isomer ca 3:1 by $^1H$ nmr spectroscopy).

EXAMPLE 3f

When the phenylselenothioether XXII was exposed to 1.1 equivalents of m-chloroperbenzoic acid in methylene chloride at −78° C. followed by another 1.1 equivalents at −20° C. and warmed to +25° C. it led selectively to the formation of the (E)-β,γ-unsaturated sulfoxide (mixture of 2 isomers) in 94% yield. A trace amount of the α,β-unsaturated sulfoxide was observed by $^1H$ nmr in some experiments.

EXAMPLE 3g

When the (E)-2,3-unsaturated sulfoxide obtained from example 3f was treated with additional mCPBA (1.1 equivalents) in $CH_2Cl_2$ at −78° C. to −25° C. for 4 hours, the (E)-2,3-unsaturated sulfone was obtained in 94% yield.

EXAMPLE 3h

When the phenylselenothioether XXII was exposed to a combination of mCPBA (2.2 equivalents at −78° C.→25° C.) followed by $H_2O_2$ (4 equival. at 25° C., 24 hours) a 95% yield of the (E)-2,3-unsaturated sulfone was obtained.

EXAMPLE 4

When the thioacetate XXIII was exposed to PheSeCl (1.2 equivalents) at −78° C. in dry methylene chloride for 1 hour followed by selective oxidation with mCPBA as in example 3f, a 94% yield of the (Z)-α,β-unsaturated sulfoxide XXIV was obtained, as a mixture of 2 isomers.

EXAMPLES 5-8

To demonstrate the generality of the ring forming reaction, a series of unsaturated thioacetates and thiols were prepared and subjected to the PhSeCl-induced cyclization process. The starting thiols or thioesters were dissolved in dry methylene chloride at −78° C. and 1.2 equivalents of PhSeCl was added and the mixture stirred for about 1 hour. After allowing the reaction mixture to come to RT, the product selenothioethers were separated by extraction and purified by column or preparative thin layer chromatography. The yields are very satisfactory. See Table II.

EXAMPLE 9

Preparation of 4(E)-9-deoxy-6,9α-epoxy-Δ$^4$-PGF$_{1α}$ (Formula VIII ($R^1$=$R^2$=$R^3$=H))

The natural form of PGF$_{2α}$ methyl ester (for formula see Table II) on exposure to PhSeCl (1.1 equiv.) in $CH_2Cl_2$ at $-78°$ C., afforded a cyclic phenylselenoether (mixture of diastereoisomers) as the major product (75%). This regio- and chemo-specific ring closure was expected on steric and proximity grounds. Conversion of the cyclic phenylselenoether into the corresponding selenoxide (1.5 equiv. of $H_2O_2$, tetrahydrofuran, $0°-25°$ C.) followed by syn elimination (25° C.), away from the oxygen to afford a trans double bond furnished the methyl ester VIII ($R^1 = $ —$CH_3$, $R^2 = R^3 = H$) in 81% yield. Saponification of the methyl ester (10 equiv. of LiOH in 3:1 MeOH-$H_2O$ at 25° C.) afforded the Lithium salt in quantitative yield. The compound was obtained as a mixture of two diastereoisomers ($6\alpha$ and $6\beta$) which could be separated by chromatography.

EXAMPLE 10

Preparation of 6,9-sulfoxa-5(E) prostacyclin, methyl ester 0.425 g of the methyl ester of 15-acetoxy $PGE_2$(VI-Z, $R^6 = $ —$CH_3$, $R^7 = $

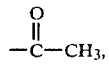

$R^8 = H$; Corey et al, P.N.A.S., USA, 72, 3355 (1975)) was dissolved in 12 ml of methylene chloride and to the solution was added 0.218 gm (1.5 equiv.) of dihydropyran and 0.46 mg (0.2 mole % equiv.) of p-toluenesulfonic acid at 25° C. After stirring for 0.5 hours, the reaction was stopped and 100% yield of the 11-THP, 15-acetoxy $PGE_2$ methyl ester was obtained (VI-Z, $R^6 = $ —$CH_3$, $R^7 = $

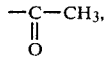

$R^8 = $ THP). 0.535 gm of the 11-THP, 15-acetoxy $PGE_2$ methyl ester thus obtained was dissolved in 12 ml of DME at 25° C. and treated with an excess (1.5 equivalents) of zinc borohydride for 15 hours. After isolation and purification, a 95% yield of a mixture of $9\alpha$ and $9\beta$-$PGF_{2\alpha}$ was obtained ($9\beta:9\alpha$ ratio=55:45). The desired $9\beta$-$PGF_{2\alpha}$ isomer (VII-Z, $R^6 = $ —$CH_3$, $R^7 = $ —$COCH_3$, $R^8 = $ THP) was obtained by chromatographic separation from the $9\alpha$ isomer on silica gel with ether as solvent. The $9\beta$-$PGF_{2\alpha}$ isomer thus obtained was then transformed into the $9\beta$ mesylate-$PGF_{2\alpha}$ methyl ester (V-Z, $R^1 = $ —$CH_3$, $R^2 = $

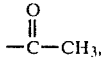

$R^3 = $ -THP, $R^5 = $ —$SO_2CH_3$). This reaction was carried out by dissolving 0.190 gm of the $9\beta$-$PGF_{2\alpha}$ methyl ester VII-Z in 4 ml of methylene chloride at $-20°$ C., adding 53 mg of methanesulfonyl chloride (1.2 equivalents) in the presence of triethylamine (1.2 equiv.). After stirring for 30 minutes, the product $9\beta$-mesylate was extracted and purified. When $9\beta$-mesylate $PGF_{2\alpha}$ methyl ester (0.190 gm) thus obtained was treated with potassium thioacetate (0.38 gm, 10 equivs.) in 2 ml of DMSO, at 45° C., for 24 hours, the thioacetate III-Z ($R^1 = $ —$CH_3$, $R^2 = $

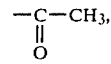

$R^3 = $ -THP, $W = $ —S—$COCH_3$) was obtained in 90% yield. Removal of the tetrahydropyranyl group $R^3$ was carried out in acetic acid-THF-water (3:2:2) at 45° for 20 hours and resulted in the formation of the diacetate III-Z ($R^1 = $ —$CH_3$, $R^2 = $

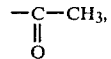

$R^3 = H$, $W = $ —S—$COCH_3$) in 98% yield. Treatment of this diacetate with anhydrous potassium carbonate (4 equivalents) in absolute methanol at 25° C. for 2 hours, gave an 83% yield of $9\alpha$-thio-$PGF_{2\alpha}$ methyl ester (III-Z, $R^1 = $ —$CH_3$, $R^2 = R^3 = H$, $W = $ —SH). Exposure of this $9\alpha$-thio $PGF_{2\alpha}$ methyl ester ($CH_2Cl_2$, $-78°$ C., 80%) to phenylselenenyl chloride (1.2 equiv.) resulted in the formation of a cyclic 5-phenylseleno, $6,9\alpha$-thiaprostacyclin methyl ester IV ($R^1 = $ —$CH_3$, $R^2 = R^3 = H$, $Z = $ —S—). This chromatographically and spectroscopically homogeneous product appears to be a single isomer and is different from the one obtained from the corresponding 4(E)-$PGF_{2\alpha}$ precursor (see example 11a). Oxidation with mCPBA of the phenyl selenide thus obtained in $CH_2Cl_2$ at 31 78° C. (1.1 equiv.) followed by another 1.1 equiv. at $-20°$ C. and warming to 25° C., led selectively to the formation of 5(E)-$6,9\alpha$-sulfoxide prostacyclin methyl ester in 95% yield.

EXAMPLE 11a

Preparation of 5(Z)-$6,9\alpha$-sulfoxaprostacyclin sodium salt

The starting material for this synthesis is 11,15-bis(tetrahydropyranyl)ether $PGF_{2\alpha}$ methyl ester (Corey, et al, J. Amer. Chem. Soc., 92, 397 (1970)). This compound was transformed to the $9\alpha$ mesylate 11,15 bis (THP) ether $PGF_{2\alpha}$ methyl ester via reaction with methanesulfonyl chloride (1.5 eqs.) in methylene chloride at $-20°$ C. for 0.5 hours. The so obtained mesylate was transformed to the $9\beta$-hydroxy epimer $PGF_{2\alpha}$ methyl ester VII-Z ($R^6 = $ —$CH_3$, $R^7 = R^8 = $ THP) with potassium superoxide (16 equivs.) in DMSO:DME (2:1) at 25° C. for 12 hours. The $9\beta$-hydroxy $PGF_{2\alpha}$ isomer ws then reacted with methanesulfonyl chloride (as in example 1), to yield to $9\beta$-mesylate V-Z ($R^1 = $ —$CH_3$, $R^2 = R^3 = $ THP, $R^5 = $ —$SO_2CH_3$) in 98% yield. This compound was then deprotected in acetic acid-THF-water (3:2:2) at 45° C. to give the diol V-Z ($R^1 = $ —$CH_3$, $R^2 = R^3 = H$, $R^5 = $ —$SO_2CH_3$) and reprotected with tert-butyldimethyl silylchloride (4 eqs.) imidazole-DMF at 25° C. to afford the $9\beta$-mesylate bis(silyl)PG-$F_{2\alpha}$ methyl ester V-Z ($R^1 = $ —$CH_3$, $R^2 = R^3 = $

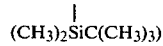

in 90% yield. Irradiation of this bis(silyl)ether with UV light (255 nm) in the presence of diphenyldisulfide (0.5 equivs.) in degassed benzene solution at 20° C. for 4 hours, gave an equilibrium mixture of 5(E)- and 5(Z)-isomers (V-E and V-Z; $R^1$, $R^2$ and $R^3$ as above). The 5(E) isomer predominated (ca 85:15). Column chromatography on silver nitrate-impregnated silica gel led to isolation of pure 5(E) mesylate V-E ($R^1$, $R^2$, $R^3$ as above), (80%). Exposure of the thus obtained intermediate V-E to excess $KSCOCH_3$ in DMSO at 45° C. for 24 hours, furnished the 9α-thioacetate III-E ($R^1$, $R^2$, $R^3$ as above,

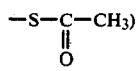

in 86% yield. On treatment with phenylselenyl chloride (1.2 equivs.) in dry methanol at −78° C. for 1 hour the thioacetate cyclized smoothly to the phenylselenothioether IV in 82% yield ($R^1$, $R^2$ and $R^3$ as above; Z=S). This chromatographically and spectroscopically homogeneous material is assumed to be a single diastereoisomer and is different from the one obtained in a similar manner from the corresponding 5(Z)-thioacetate PGF$_{2\alpha}$ methyl ester III-Z ($R^1$, $R^2$, $R^3$ as above, W=—SCOCH$_3$). When the selenothioether IV ($R^1$, $R^2$, $R^3$ as above, Z=—S—) was heated in acetic acid-THF-H$_2$O (3:2:2) at 45° C. for 15 hours, desilylation occurred and the diol thioether IV ($R^1$=—CH$_3$, $R^2$=$R^3$=H, Z=—S—) was formed quantitatively.

The selenothioether thus obtained gave, on treatment with 2.2 equivalents of m-chloroperbenzoic acid in methylene chloride at −78°→0° C. the 6,9α-sulfoxaprostacyclin methyl ester IX (n=1, $R^1$=—CH$_3$, $R^2$=$R^3$=H) quantitatively and as a mixture of 2 isomers. These isomers can be easily separated by preparative layer chromatography on silica gel (5% methanol in CH$_2$Cl$_2$) to give pure sulfoxides.

The sulfoxide methyl ester was then hydrolyzed in 90% ethanol with sodium hydroxide at 25° to afford a stable solution of the sodium salt IX ($R^1$=Na). Acidification of this compound in aqueous solutions leads to the corresponding acid which can be extracted with ether and purified chromatographically.

EXAMPLE 11b

Preparation of 5(Z)-6,9α-thiaprostacyclin methyl ester

Reduction of the 5(Z)-6,9-sulfoxaprostacyclin methyl ester obtained in example 10a, with excess iodotrimethylsilane in CCl$_4$ with addition of 4 equiv. of pyridine at 0° C. for 0.5 hours, lead to 5(Z)-6,9α-thiaprostacyclin methyl ester, a highly active analog of natural prostacyclin. The sodium salt could be obtained by base hydrolysis.

EXAMPLE 11c

Preparation of 5(Z)-6,9α-sulfoprostacyclin sodium salt

The critical intermediate for this synthesis is 11,15-diol, 5-phenylseleno, 6,9α-thiaprostacyclin methyl ester IV ($R^1$=—CH$_3$, $R^2$=$R^3$=H, Z=—S—). The preparation of this intermediate is described in Example 10a. When this intermediate was oxidized with 3.3 equivalents of m-chloroperbenzoic acid in methylene chloride −78°→20° C. for 24 hours, the 6,9α-sulfoprostacyclin methyl ester IX was produced in 85% yield (IX, $R^1$=—CH$_3$, $R^2$=$R^3$=H, n=2). It was isolated by prep layer chromatography and hydrolyzed with NaOH in 90% ethanol at 25° C. to afford the corresponding sodium salt IX. The salt was quantitatively stable in aqueous solution and gave, by acidification, the corresponding acid which could be extracted with ether and purified chromatographically.

Analytical data for methyl ester: $^1$H nmr: 220 MHz, CDCl$_3$, τ4.04 (t, J=8 Hz, 1H, sulfoenol ether); τ4.43 (dd, J=15.5 Hz, 7 Hz, 1H, olefin); τ4.60 (dd, J=15.5, 8 Hz, 1H, olefin); i.r. spectra: CHCl$_3$, νmax (1120, 1300 cm$^{-1}$ sulfone) (1725 cm$^{-1}$, ester) solubility: common organic solvents.

EXAMPLE 11d

Preparation of 4(E) 6,9α-sulfoisoprostacyclin

The critical intermediate for this synthesis is the 11,15 diol, 5-phenylseleno, 6,9α-thiaprostacyclin methyl ester IV ($R^1$=—CH$_3$, $R^2$-$R^3$=H, W=—S—). The preparation of this intermediate is described in Example 10a. When this intermediate was treated with 2.2 equivalents of m-chloroperbenzoic acid at −78°-20° C. followed by 8 equivalents of H$_2$O$_2$ at 25° C. for 24 hours in THF, 32% yield of the unconjugated 6,9-sulfo-4(E) isoprostacyclin methyl ester was produced. The material could be separated and purified by prep layer chromatography on silica gel, (2.5% methanol in ether, R$_f$=0.06). Base hydrolysis of the methyl ester as described for Examples 2 and 3 supra, afforded the corresponding sodium salt.

Analytical data for methyl ester: $^1$H n.m.r.: τ4.15 (ill defined doublet, J=15.5 Hz, 1H, olefin); τ4.52 (m, 3H, olefinic); i.r.: CHCl$_3$, νmax (1125, 1310 cm$^{-1}$ sulfone), (1735 cm$^{-1}$, ester) solubility: CH$_2$Cl$_2$ and common organic solvents.

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A method of preparing a prostacyclin derivative of the formula (1):

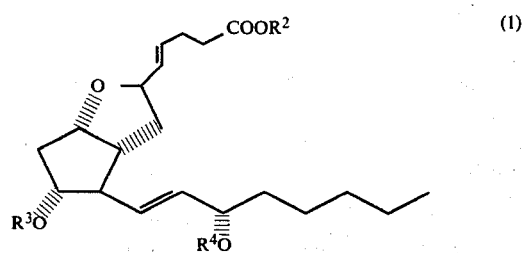

wherein $R^2$ is any pharmaceutically acceptable cation or lower alkyl group having 1 to 4 carbon atoms, $R^3$ and $R^4$ are hydrogen or acid-labile or base-labile hydroxy protecting groups; which comprises:

cyclizing a PGF$_{2\alpha}$ prostaglandin derivative with a selenenyl halide of the formula $R^1$Se-halide wherein $R^1$ is selected from the group consisting of phenyl, lower alkyl and alkyl substituted phenyl; wherein the molar ratio of said selenenyl halide to said PGF$_{2\alpha}$ derivative is 0.9–1.5 to 1, thereby obtaining a selenoether intermediate of the formula (2):

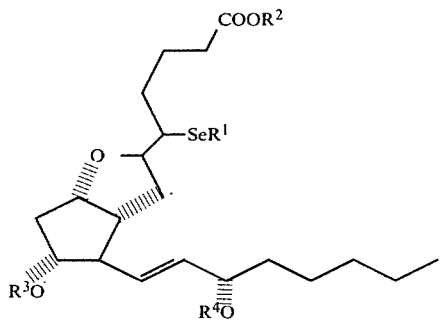

reacting said selenoether intermediate (2) with an oxidizing agent; and when $R^3$ and $R^4$ are different than hydrogen, removing said protecting groups $R^3$ and $R^4$ in acid or base.

2. The method of claim 1 wherein $R^3$ and $R^4$ are hydrogen.

3. The method of claim 1 wherein $R^1$ is phenyl.

4. The method of claim 1 wherein $R^2$ is —$CH_3$.

5. The method of claim 1 wherein $R^2$ is Na.

6. The method of claim 1 wherein said $PGF_{2\alpha}$ derivative is 5(Z)-11,15-diacetyl, $PGF_{2\alpha}$ methyl ester.

7. The method of claim 1 wherein said cyclization is carried out in methylene chloride as solvent.

8. The method of claim 1 wherein said cyclization is carried out at a temperature of −78° C.

9. A method of preparing a selenoether intermediate of formula (I):

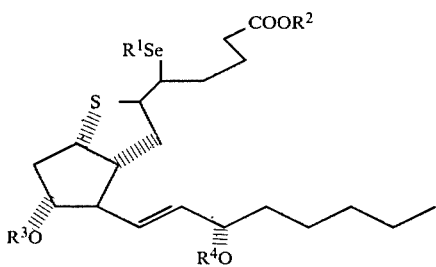

wherein $R^1$ is selected from the group consisting of phenyl, lower alkyl, and alkyl substituted phenyl, $R^2$ is any pharmaceutically acceptable cation or lower alkyl group having 1 to 4 carbon atoms, and $R^3$ and $R^4$ are hydrogen or acid-labile or base-labile hydroxy protecting groups, which comprises:

cyclizing a material selected from the group consisting of a 9α-thio analogue of a $PGF_{2\alpha}$ prostaglandin derivative or a 9α-thioester analogue thereof, with a selenenyl halide of formula $R^1Se$ halide, wherein the molar ratio of said selenenyl halide to said prostaglandin analogue is 0.9 to 1.5–1.

10. The method of claim 9 wherein $R^1$ is phenyl.

11. The method of claim 9 wherein $R^3$ and $R^4$ are hydrogen.

12. The method of claim 9 wherein said $PGF_{2\alpha}$ prostaglandin analogue is a 9α-thio analogue.

13. The method of claim 9 wherein said $PGF_{2\alpha}$ prostaglandin analogue is a 9α-thioester analogue and $R^3=R^4=$tert-butyl dimethyl silyl.

14. The method of claim 13 wherein said thioester $PGF_{2\alpha}$ analogue is 5(E)-9α-thioacetyl $PGF_{2\alpha}$ methyl ester.

15. The method of claim 12 wherein said thio analogue is 5(E)-9α-thio $PGF_{2\alpha}$ methylester.

16. The method of claim 9 wherein said cyclization is carried out in methylene chloride as a solvent.

17. The method of claim 9 wherein said cyclization is carried out at a temperature of about −78° C.

18. A method of preparing a sulfoxide analogue of prostacyclin of the formula (II):

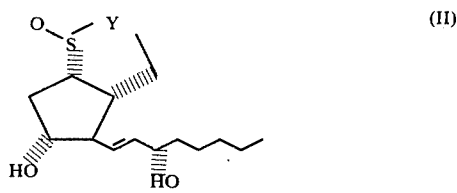

wherein Y is (E) or (Z)>C=CH—$CH_2CH_2CH_2COOR^2$ respectively, which comprises:

reacting the 5Z or 5E isomer respectively of a 9α-thioether analogue of a $PGF_{2\alpha}$ prostaglandin derivative, with a selenenyl halide of formula $R^1Se$ halide, wherein the molar ratio of said selenenyl halide to said prostaglandin analogue is 0.9 to 1.5–1, thereby obtaining a selenoether intermediate of formula (I):

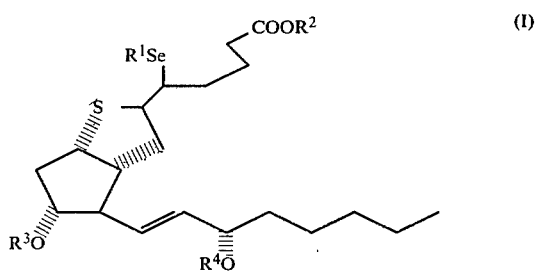

wherein $R^1$ is selected from the group consisting of phenyl, lower alkyl, and alkyl substituted phenyl, $R^2$ is any pharmaceutically acceptable cation or lower alkyl group having 1 to 4 carbon atoms, and $R^3$ and $R^4$ are hydrogen or acid-labile or base-labile hydroxy protecting groups;

treating the selenoether intermediate I with about stoichiometric amounts of an oxidizing agent selected from the group consisting of m-chloroperbenzoic acid, hydrogen peroxide and mixtures thereof and, when $R^3$ and $R^4$ in said intermediate (I) are different than hydrogen, removing said protecting groups $R^3$ and $R^4$ in acid or base.

19. The method of claim 18 wherein Y=(Z)>C=CH—$CH_2CH_2CH_2COOCH_3$.

20. The method of claim 18 wherein Y=(Z)>C=CH—$CH_2CH_2CH_2COONa$.

21. A method of preparing sulfoxide or sulfone prostacyclin analogues of the formula (III):

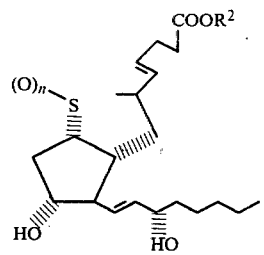

wherein n=1 or 2; which comprises:
reacting a material selected from the group consisting of a 9α-thio analogue of a PGF$_{2α}$ prostaglandin derivative or a 9α-thioester analogue thereof, with a selenenyl halide of formula R$^1$Se halide, wherein the molar ratio of said selenenyl halide to said prostaglandin analogue is 0.9 to 1.5–1;
thereby obtaining a selenoether intermediate of formula (I):

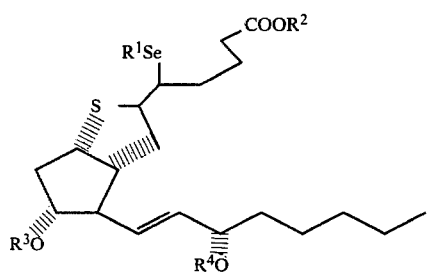

wherein R$^1$ is selected from the group consisting of phenyl, lower alkyl and alkyl-substituted phenyl, R$^2$ is any pharmaceutically acceptable cation or lower alkyl group having 1 to 4 carbon atoms, and R$^3$ and R$^4$ are hydrogen or acid-labile or base-labile hydroxy protection groups,
treating the selenoether intermediate I with about stoichiometric amounts of hydrogen peroxide; and
when R$^3$ and R$^4$ are different than hydrogen in said selenoether intermediate I, removing the protecting groups R$^3$ and R$^4$ in acid or base.

22. The method of claim 21 wherein n=2 and R$^2$=CH$_3$.

23. The method of claim 21 wherein n=2 and R$^2$=Na.

24. A method of preparing sulfone analogues of prostacyclin of the formula:

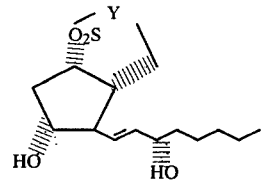

wherein Y is respectively (E) or (Z)>C=CH—CH$_2$CH$_2$CH$_2$COOR$^2$, which comprises:
reacting the 5Z or 5E isomers respectively of a material selected from the group consisting of a 9α-thio analogue of a PGF$_{2α}$ prostaglandin derivative or a 9α-thioester analogue thereof, with a selenenyl halide of formula R$^1$Se halide, wherein the molar ratio of said selenenyl halide to said prostaglandin analogue is 0.9 to 1.5–1; thereby obtaining a selenoether intermediate of formula (I):

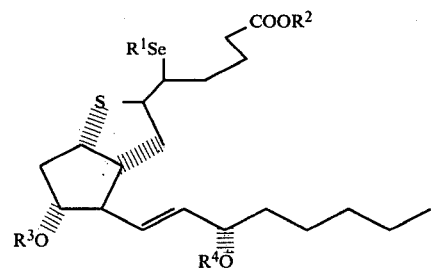

wherein R$^1$ is selected from the group consisting of phenyl, lower alkyl, and alkyl-substituted phenyl, R$^2$ is any pharmaceutically acceptable cation or lower alkyl group having 1 to 4 carbon atoms, and R$^3$ and R$^4$ are hydrogen or acid-labile or base-labile hydroxy protecting groups,
treating the selenoether intermediate I, with a stoichiometric excess of an oxidizing agent selected from the group consisting of m-chloroperbenzoic acid, hydrogen peroxide and mixtures thereof; and
when R$^3$ and R$^4$ are different than hydrogen in said selenoether intermediate I, removing the protecting groups R$^3$ and R$^4$ in acid or base.

25. The method of claim 24 wherein Y=(Z)>C=CH—CH$_2$CH$_2$CH$_2$COOCH$_3$.

26. The method of claim 24 wherein Y=(Z)>C=CH—CH$_2$CH$_2$CH$_2$COONa.

* * * * *